United States Patent [19]

Takeuchi et al.

[11] Patent Number: 5,756,552
[45] Date of Patent: *May 26, 1998

[54] LYOPHILIZED PHARMACEUTICAL PREPARATIONS CAPABLE OF PROVIDING AQUEOUS DRUG COMPOSITION HAVING PROPERTY OF REVERSIBLE THERMOSETTING GELATION

[75] Inventors: Masanobu Takeuchi; Hiroe Suzuki; Toshie Takahashi; Hiroki Maruyama; Miyako Sasaki; Keiko Naito; Touru Oguma; Makoto Maeda, all of Nihonbashi-Muromachi, Japan

[73] Assignee: Wakamoto Pharmaceutical Co., Ltd., Tokyo, Japan

[*] Notice: The term of this patent shall not extend beyond the expiration date of Pat. No. 5,624,962.

[21] Appl. No.: 809,604

[22] PCT Filed: Oct. 13, 1994

[86] PCT No.: PCT/JP94/01709

§ 371 Date: Apr. 14, 1997

§ 102(e) Date: Apr. 14, 1997

[87] PCT Pub. No.: WO96/11672

PCT Pub. Date: Apr. 25, 1996

[51] Int. Cl.$^6$ .............................. A61K 9/08; A61K 47/36

[52] U.S. Cl. .................. 514/772.2; 514/781; 514/784
[58] Field of Search ............................ 514/781, 784, 514/772.4, 772.2

[56] References Cited

U.S. PATENT DOCUMENTS 5,624,962  4/1997  Takeuchi et al. ................ 514/772.2

Primary Examiner—Gary L. Kunz
Attorney, Agent, or Firm—Oblon, Spivak, McClelland, Maier & Neustadt, P.C.

[57] ABSTRACT

Herein disclosed is a lyophilized pharmaceutical preparation obtained by lyophilizing an aqueous composition having property of reversible thermosetting gelation and comprising an effective amount of a drug, 0.2 to 2.1 (W/V)% of methylcellulose (the content of methoxyl group is within the range of 26 to 33%), 1.2 to 2.3 (w/v)% of citric acid and 0.5 to 13 (W/V)% of polyethylene glycol. The lyophilized pharmaceutical preparation makes it possible to stably store drugs unstable to water till they are put into practical use and, upon therapeutic use, an aqueous composition having property of reversible thermosetting gelation which can undergo gelation when locally applied can easily and immediately be reconstituted from the preparation by addition of a proper amount of a solvent for reconstitution.

14 Claims, No Drawings

LYOPHILIZED PHARMACEUTICAL PREPARATIONS CAPABLE OF PROVIDING AQUEOUS DRUG COMPOSITION HAVING PROPERTY OF REVERSIBLE THERMOSETTING GELATION

TECHNICAL FIELD

The present invention relates to a lyophilized pharmaceutical preparation which can provide an aqueous drug composition having property of reversible thermosetting gelation when reconstituted with a solvent for reconstitution. The aqueous drug composition having property of reversible thermosetting gelation reconstituted from the lyophilized pharmaceutical preparation is characterized in that the aqueous drug composition is a fluid liquid at room temperature or lower and, when administered to eyes or body cavities or spreaded on skin, gelation happens at body temperature of mammal, so as to achieve a greater degree of bioavailability of the pharmacologically effective component and maintain the effect of the drugs for long period.

BACKGROUND ART

The pharmaceutical preparation having property of reversible thermosetting gelation which causes a sol-gel transition at the drug-administered site exhibits various advantages such as improvement in the drug delivery and patient's compliance as compared with the conventional pharmaceutical preparations.

Hitherto, there have been proposed several aqueous drug compositions which are liquid at room temperature or lower and form a semi-solid or gel at body temperature of mammal, as aqueous drug compositions which effectively release a pharmacologically effective component to mammal to be treated. U.S. Pat. No. 4,188,373 discloses an aqueous composition having property of thermosetting gelation, which comprises PLURONIC (trademark) and form gel by application of heat, and a desired sol-gel transition temperature thereof is obtained by controlling the concentration of PLURONIC. Moreover, U.S. Pat. Nos. 4,474,751, 4,474,752, 4,474,753 and 4,478,822 disclose drug delivery systems utilizing aqueous drug compositions having property of thermosetting gelation.

The inventors of this invention already provided a drug composition having property of reversible thermosetting gelation for treating eyes, body cavities and skin which comprises an effective amount of a drug used for pharmacological therapy or diagnosis, methylcellulose, citric acid and polyethylene glycol and whose pH ranges from 3 to 10, wherein the composition is a highly fluid liquid prior to administration or application and undergoes gelation immediately after administration or application thereof due to the temperature of the site to which the composition is administered or spreaded (PCT/JP93/01636).

However, it is difficult to store the foregoing aqueous composition over a long time period, since in case where an drug unstable to water is applied to the composition, the drug undergo decomposition, although the composition exhibits satisfactory effects such as enhancement of the bioavailability of the drug and the long acting drug efficacy.

Accordingly, an object of the present invention is to provide an aqueous drug composition having property of reversible thermosetting gelation which can be applied to drugs unstable to water, as well.

DISCLOSURE OF INVENTION

The present inventors have diligently conducted many researches in order to develop an aqueous drug composition which can be applied to drugs unstable to water as well and, as a result, have found out that a drug can be formed into a pharmaceutical preparation by incorporating, into the drug, appropriate amounts of methylcellulose, citric acid and polyethylene glycol and then lyophilizing the resulting mixture, even if the drug is unstable to water and thus have completed the present invention.

That is, the present invention provides a lyophilized pharmaceutical preparation which is prepared by lyophilizing an aqueous composition having property of reversible thermosetting gelation comprising an effective amount of a drug used for pharmacological therapy or surgical operations, 0.2 to 2.1 (W/V)% of methylcellulose (the content of methoxyl group is within the range of 26 to 33%), 1.2 to 2.3 (W/V)% of citric acid and 0.5 to 13 (W/V)% of polyethylene glycol (PEG) (wherein (W/v)% means weight/volume %).

One of the excellent advantageous features of the lyophilized pharmaceutical preparation according to the present invention is that it can stably store an unstable drug till the drug is practically used and that it can immediately reconstitute an aqueous composition having property of reversible thermosetting gelation by adding a proper amount of a solvent for reconstitution when it is used for treatment. The aqueous composition thus reconstituted is a highly fluid liquid prior to the administration or application, causes gelation immediately after the administration or application due to body temperature of the site to which the composition is administered or applied to thus ensure an increase in the bioavailability of the effective component and a long acting drug efficacy.

Any methylcellulose products can be used alone or as a mixture thereof as the methylcellulose (content of methoxyl group: 26–33%) component used in the lyophilized pharmaceutical preparation of the present invention, so long as they have a viscosity of 2% aqueous solution within the range of 13 to 12,000 millipascal·sec at 20° C. The content of methoxyl group is preferably within the range of from 26 to 33% in view of the solubility in water. Such methylcellulose products are sold by Shin-Etsu Chemical Co., Ltd. as METOLOSE™ SM 15, SM 25, SM 100, SM 400, SM 1500, SM 4000, SM 8000 (each numerical value represents the viscosity of 2% aqueous solution as determined at 20° C. and expressed in terms of millipascal. sec), and by Matsumoto Oil and Fat Pharmaceutical Industry Inc. as MARPOLOSE™ M, and by Dow chemical Co. as METOCEL™ A, and all commodities can be easily available.

PEG's used in the lyophilized pharmaceutical preparation of the present invention are sold by Wako Junyaku Industry Inc. as PEG-200, PEG-300, PEG-600, PEG-1000, PEG-1540, PEG-2,000, PEG-4,000, PEG-6,000, PEG-20,000, PEG-50,000, PEG-500,000, PEG-2,000,000and PEG-4,000,000, and by Nippon Oil and Fats Co., Ltd. as MACROGOL-200, MACROGOL-300, MACROGOL-400, MACROGOL-600, MACROGOL-1,500, MACROGOL-1,540, MACROGOL-4,000, MACROGOL-6,000 and MACROGOL-20,000.

The weight-average molecular weight of PEG used in the present invention is preferably 1000 to 50,000. This is because if the weight-average molecular weight is less than 1000, the resulting composition tends to be hard to form gel at a local region, while if it is more than 50,000, the viscosity thereof in the liquid state is too high. Two or more kinds of PEG can be mixed to adjust the weight-average molecular weight thereof so as to fall within the above optimum range.

The concentration of the methylcellulose used in the present invention is within the range of 0.2 to 2.1 (W/v)%.

This is because if the concentration of methylcellulose is less than 0.2 (W/V)%, the resulting composition becomes hard to form gel at a local region and, while if it is more than 2.1 (W/V)%, the composition shows unduly high viscosity in the sol state which makes the dosage thereof incorrect.

The concentration of the citric acid is within the range of 1.2 to 2.3 (W/V)%. This is because if the concentration of citric acid is less than 1.2 (W/V)%, the resulting composition becomes hard to form gel at a local region, while the use thereof in an amount of more than 2.3 (W/V)% is not preferred in view of the stimulus on the composition-administered site.

The concentration of PEG is within the range of 0.5 to 13 (W/v)%. This is because if the concentration of PEG is less than 0.5 (W/V)%, the resulting composition becomes hard to form gel at a local region and hence loses practical value, while if the concentration is more than 13 (w/v)%, the composition shows high viscosity in the sol state.

The lyophilized pharmaceutical preparation of the present invention may be used for treating diseases of, for example, eyes, skin and body cavities. Examples of medicines which can be incorporated into the lyophilized pharmaceutical preparation of the present invention and administered to eyes of mammal, are as follows: antiviral agents such as adenosine arabinoside and interferons; antifungal agents such as Amphotericin B and Nystatin; antibacterial substances such as Sodium Carbenicillin, Potassium Penicillin G, Sodium Cefazolin, Tetracycline Hydrochloride, Polymyxin B, Vancomycin Hydrochloride, Amikacin Sulfate and Erythromycin Lactobionate; antiallergic agents such as Aspirin; anti-inflammatory agents such as Indomethacin; miotics such as Acetylcholine Chloride and Physostigmine Salicylate; vitamins such as Cocarboxylase and Cobamamide; antiglaucoma drugs such as Dipivefrine; anticataract drugs such as Glutathione and Pirenoxine; carbonic anhydrase inhibitors such as Acetazolamide; immunosuppressive agents such as Methotrexate and Cyclophosphamide; amino acids such as cysteine; adjuvants for surgery such as hyaluronidase and α-Chymotrypsin; and anti-proliferative agents for fibroblast such as Mitomycin C.

Examples of medicines which can be incorporated into the lyophilized pharmaceutical preparation of the present invention and applied to sites or skin of mammal, are as follows: antifungal agents such as Nystatin; antibacterial substances such as Tetracycline Hydrochloride, Polymyxin B, Amikacin Sulfate and Erythromycin Lactobionate; and anti-inflammatory agents such as Aspirin and Indomethacin.

Examples of drugs which can be incorporated into the lyophilized pharmaceutical preparation of the present invention and administered to body cavities of mammal, that is, rectum, urethra, nasal cavity, vagina, auditory meatus, oral cavity and buccal pouch, are as follows: antiviral agents such as interferons; antifungal agents such as Nystatin; antibacterial substances such as Tetracycline Hydrochloride, Amikacin Sulfate and Erythromycin; antipyretics such as Aspirin; analgesics such as Aspirin and Indomethacin; anti-inflammatory agents such as Indomethacin; and antineoplastics such as Doxorubicin and Asparaginase.

The content of the effective drug in the lyophilized pharmaceutical preparation may vary depending on the kinds of the drugs selected, but it is generally preferred that the composition reconstituted from the lyophilized preparation contains the effective drug in an amount ranging from about 0.001% to 5% by weight based on the composition.

Examples of pH-adjusting agents used in the present invention include acids such as hydrochloric acid, sulfuric acid, boric acid, phosphoric acid and acetic acid and bases such as sodium hydroxide, monoethanolamine, diethanolamine and triethanolamine.

In the invention, water is generally used as the solvent for reconstitution of the pharmaceutical preparation, but it may, if necessary, comprise pharmaceutically acceptable additives such as buffering agents, preservatives and solubilizing agents. Examples of such preservatives may include invert soaps such as benzalkonium chloride and chlorhexidine gluconate, parabens such as methylparaben, ethylparaben, propylparaben and butylparaben, alcohols such as chlorobutanol, phenylethyl alcohol and benzyl alcohol and organic acids such as dehydroacetic acid, sorbic acid and salts thereof. Moreover, surfactants or chelating agents may, if necessary, be added to the reconstitution solvent. Generally, these components may be used within the range of about 0.001 to 2% by weight, and preferably within the range of about 0.002 to 1% by weight. Examples of such buffering agents include alkaline metal salts of acids such as phosphoric acid, boric acid, acetic acid, tartaric acid, lactic acid and carbonic acid, amino acids such as glutamic acid, ε-aminocaproic acid, aspartic acid, glycine, arginine and lysine, taurine and trisaminomethane. These buffering agents may be added to the reconstitution solvent in an amount required for maintaining the pH of the solvent within the range of 3 to 10. Examples of such solubilizing agents include POLYSORBATE 80 and polyoxyethylene hydrogenated castor oil and they may be used in an amount ranging from 0 to 5% by weight.

According to the present invention, a desired lyophilized pharmaceutical preparation can be obtained by preparing an aqueous composition comprising an effective amount of a drug, 0.2 to 2.1 (W/V)% of methylcellulose, 1.2 to 2.3 (W/V)% of citric acid, 0.5 to 13 (W/V)% of polyethylene glycol and a pH adjusting agent in an amount required for controlling the pH of the composition to 3 to 10; and then lyophilizing the aqueous composition by the method currently used. The method for preparing the lyophilized pharmaceutical preparation of the present invention is not restricted to specific ones and, for example, comprises dissolving a citrate and PEG in sterilized and purified water, adjusting the pH of the resulting solution with a pH adjusting agent, adding, if necessary, a variety of additives such as a buffering agent and a preservative, adding a solution of methylcellulose in sterilized and purified water and then ice-cooling the solution. Then a drug is added to the solution, followed by again adjusting the pH thereof, filling up the volume of the mixture with sterilized and purified water and dissolving the mixture while stirring it with ice-cooling. Thereafter, the resulting solution is divided into equal volume portions and dispensed into proper containers and then lyophilized in a freeze dryer according to the usual method which comprises, for instance, freezing the dispensed solution at about −40° C. to about −60° C. and sublimating the ice under a reduced pressure of not more than 0.3 mmHg to thus give a lyophilized pharmaceutical preparation. In this respect, if the drug used is hardly soluble or insoluble in water, it is lyophilized after suspending it in water or solubilized therein using a solubilizing agent.

In the method for preparing the lyophilized pharmaceutical preparation of the present invention including the foregoing lyophilization step, methylcellulose, citric acid and polyethylene glycol as main components do not undergo any substantial change (decomposition or deterioration) and accordingly, the lyophilized pharmaceutical preparation of the present invention comprises methylcellulose in an amount ranging from about 1 to about 50% by weight, preferably 1.5 to 34% by weight; citric acid or a salt thereof in an amount ranging from about 5 to about 60% by weight, preferably 7.2 to 38% by weight (expressed in terms of the reduced amount of citric acid); polyethylene glycol in an amount ranging from about 3 to about 88% by weight, preferably 7.0 to 82% by weight; and a drug in an amount of about 0.004 to about 70% by weight (in a case where the aqueous composition prior to the lyophilization comprises the drug in an amount ranging from 0.001 to 5% by weight).

The composition reconstituted from the lyophilized pharmaceutical preparation of the present invention must be in a liquid state at room temperature or lower and must undergo gellation at body temperature of mammal. Therefore, the gelling temperature thereof preferably ranges from about 20° C. to about 40° C. However, the reconstituted aqueous composition has a gelling temperature ranging from about 20° C. to about 40° C. so far as the concentrations of methylcellulose, citric acid and polyethylene glycol in the aqueous composition prior to the lyophilization fall within the ranges defined above, respectively.

When using the lyophilized pharmaceutical preparation of the present invention, it is dissolved in water or a solvent for reconstitution in an amount approximately identical to that of the water evaporated during the lyophilization to thus reconstitute an aqueous drug composition having property of reversible thermosetting gelation which is ready for practical use. The method for reconstituting the preparation is not restricted to specific ones and comprises, for instance, adding sterilized and purified water or, if necessary, a solvent for reconstitution containing a variety of additives to the preparation and then ice-cooling to dissolve the same.

BEST MODE FOR CARRYING OUT THE INVENTION

The following examples are provided to illustrate a variety of embodiments of the present invention and are not intended to limit the scope of the present invention. In Table 1 given below, there are listed the compositions of the aqueous drug compositions having property of reversible thermosetting gelation used in the following Examples in which the lyophilized pharmaceutical preparations of the present invention are prepared and the gelling temperatures thereof, the conditions for reconstitution of the preparations, the gelling temperatures of the reconstituted compositions, or the like.

Example 1

There were dissolved, in 50 ml of sterile purified water, 2.3 g of citric acid and 2.0 g of POLYETHYLENE GLYCOL 4000 (weight-average molecular weight: 3000; available from Nippon Oil and Fats Co., Ltd.) and then the pH of the resulting solution was adjusted to 7.0 with a 3N sodium hydroxide solution. A solution of 0.7 g of METOLOSE SM 400 (available from Shin-Etsu Chemical Co., Ltd.) and 0.7 g of METOLOSE SM 15 (available from Shin-Etsu Chemical Co., Ltd.) in 25 ml of sterile purified water was added to the solution and the mixture was sufficiently stirred with ice-cooling. Then, the pH thereof was adjusted to 8.0 with a 3N sodium hydroxide solution, 0.04 g of Mitomycin C was then added to the solution, the volume of the solution was filled up to 100ml with sterile purified water and the components were dissolved by sufficiently stirring with ice-cooling. The resulting solution was dispensed into vials (1 ml each), frozen at −50° C. in a freeze dryer and lyophilized at a reduced pressure of 0.2 to 0.02 mmHg to give an eye drop.

The foregoing eye drop was reconstituted by adding 1 ml of sterile purified water thereto and ice-cooling to dissolve it therein.

Example 2

In 50 ml of sterile purified water, there were dissolved 3.5 g of trisodium citrate dihydrate and 2.0 g of POLYETHYLENE GLYCOL 4000. A solution of 0.7 g of METOLOSE SM 400 and 0.7 g of METOLOSE SM 15 in 25 ml of sterile purified water was added to the solution and the mixture was sufficiently stirred with ice-cooling. Then, 0.5 g of Amphotericin B was added to the mixture, the pH thereof was adjusted to 8.0 with a 1N hydrochloric acid solution or a 1N sodium hydroxide solution, the volume of the mixture was filled up to 100 ml with sterile purified water and the components were dissolved by sufficiently stirring with ice-cooling. The resulting solution was dispensed into vials (1 ml each), frozen at −50° C. in a freeze dryer and lyophilized at a reduced pressure of 0.2 to 0.02 mmHg to give an eye drop.

The foregoing eye drop was reconstituted by adding 1 ml of sterile purified water thereto and then ice-cooling.

Examples 3–5

By a method similar to that described in Example 2, solutions each having a composition shown in Table 1 were prepared and then lyophilized to give eye drops. The eye drops each was reconstituted by the method similar to that used in Example 2.

Example 6

By a method similar to that described in Example 2, a solution having a composition shown in Table 1 was prepared and then lyophilized to give an eye drop. The eye drop thus obtained was reconstituted by adding 1 ml of sterile purified water containing 0.17 W/V % of boric acid, 0.11 W/V % of borax and 0.2 w/v % of polyoxyethylene hydrogenated castor oil 60 and then ice-cooling.

Example 7

By a method similar to that described in Example 2, solutions each having a composition shown in Table 1 were prepared and then lyophilized to give an eye drop. The eye drop thus obtained was reconstituted by the method similar to that used in Example 2.

Example 8

By a method similar to that described in Example 2, a solution having a composition shown in Table 1 was prepared and then lyophilized to give an eye drop. The eye drop thus prepared was reconstituted by adding 1 ml of sterile purified water containing 0.005 W/V % of benzalkonium chloride and ice-cooling to dissolve it therein.

Example 9

By a method similar to that described in Example 2, a solution having a composition shown in Table 1 was prepared and then lyophilized to give an eye drop. The eye drop thus prepared was reconstituted by adding 1 ml of sterile purified water containing 0.026 W/V % of methylparaben and 0.014 W/V % of propylparaben and ice-cooling to dissolve it in the water.

Examples 10–16

By a method similar to that described in Example 2, solutions each having a composition shown in Table 1 were prepared and then lyophilized to give eye drops. The eye drops each was reconstituted by a method similar to that used in Example 2.

Example 17–20

By a method similar to that described in Example 1, solutions each having a composition shown in Table 1 were prepared and then lyophilized to give eye drops. The eye drops each was reconstituted by a method similar to that used in Example 1.

Examples 21

By a method similar to that described in Example 2, a solution having a composition shown in Table 1 was prepared and then lyophilized to give an agent for dermal use. The agent was reconstituted by a method similar to that used in Example 2.

Examples 22

By a method similar to that described in Example 2, a solution having a composition shown in Table 1 was prepared and then lyophilized to give an agent for body cavitical use. The agent was reconstituted by a method similar to that used in Example 2.

Stability

Samples of the lyophilized pharmaceutical preparations prepared in Examples 1, 3, 4, 6, 8, 9, 21 and 22 and the corresponding aqueous compositions prior to the lyophilization as comparative samples each was stored at 40° C. for one month. Then the amounts of each drug present in the corresponding lyophilized pharmaceutical preparation and the aqueous composition were determined by the high performance liquid chromatography (HPLC) technique immediately after the preparation thereof and after the completion of the storage test to determine the rate of residual drug. The results are summarized in the following Table 2. The results clearly indicate that the lyophilized pharmaceutical preparations were substantially improved in the stability of the drugs incorporated therein as compared with that of the drugs present in the compositions prior to the lyophilization.

The quantitative analysis of each drug by the HPLC technique was performed under the following conditions. Column: CHEMCOSORB (5-ODS; available from Chemco Company) of 4 mm (inner diameter)×150 mm (length), mobile phase: a mixed liquid comprising 1/300M phosphate buffer (pH 7.0)/methanol=8/3, flow rate: 0.9 ml/min, detection: UV 254 nm, and the amount of the sample injected: 20 μl for the quantitative analysis of Mitomycin C; column: μ-Bondapak C18 (available from Waters Company) of 3.9 mm (inner diameter)×300 mm (length), mobile phase: a mixed liquid comprising 0.005M acetate buffer (pH 4.5) /methanol=4/1, flow rate: 1.0 ml/min, detection: UV 220 nm, and the amount of the sample injected: 10 μl for the quantitative analysis of Sodium Carbenicillin; column: μ-Bondapak C18 (available from Waters Company) of 3.9 mm (inner diameter)×300 mm (length), mobile phase: a mixed liquid comprising 0.007M phosphoric acid/ methanol=7/3, flow rate: 1.3 ml/min, detection: UV 254 nm, and the amount of the sample injected: 10 μl for the quantitative analysis of Cefazolin Sosium; column: LiChrospher 100RP-18 (available from E. Merck Company) of 4 mm (inner diameter)×250 mm (length), mobile phase: a mixed liquid comprising methanol/1% acetic acid=3/1, flow rate: 1.0 ml/min, detection: UV 265 nm, and the amount of the sample injected: 10 μl for the quantitative analysis of Indometacin; column: ASAHIPACK GS-320 (available from Asahi Chemical Industry Co., Ltd.) of 7.6 mm (inner diameter)×500 mm (length), mobile phase: 0.04M EDTA·3Na (pH 8.0), flow rate: 1.0 ml/min, detection: post-labeling with o-phthalaldehyde (excitation wavelength 350 nm, fluorescent wavelength 420 nm), and the amount of the sample injected: 5 μl for the quantitative analysis of Glutathion; column: LiChrosorb RP-18 (available from E. Merck Company) of 4 mm (inner diameter)×150 mm (length), mobile phase: a mixture of a solution of 1.39 g of tetra-n-butyl ammonium chloride and 4.5 g of disodium hydrogen phosphate in 1000 ml of water (pH was controlled to 6.5 with phosphoric acid)/acetonitrile/tetrahydrofuran= 70/20/3, flow rate: 1.0 ml/min, detection: UV 230 nm, and the amount of the sample injected: 10 μl for the quantitative analysis of Pirenoxine; LiChrosorb RP-8 (available from E. Merck Company) of 4.6 mm (inner diameter)×250 mm (length), mobile phase: a mixture of 0.1M ammonium oxalate/dimethylformamide/0.2M ammonium phosphate= 68/27/5 (pH was controlled to 7.6 to 7.7 with 3N phosphoric acid or 3N ammonium hydroxide), flow rate: 2.0 ml/min, detection: UV 280 nm, and the amount of the sample injected: 10 μl for the quantitative analysis of Tetracycline hydrochloride; and LiChrosorb RP-8 (available from E. Merck Company) of 4.6 mm (inner diameter)×250 mm (length), mobile phase: a mixed liquid of methanol/water/ acetic acid=43/36/1, flow rate: 1.6 ml/min, detection: UV 285 nm, and the amount of the sample injected: 10 μl for the quantitative analysis of Aspirin.

Effects of the Invention

According to the present invention, an aqueous drug composition having property of reversible thermosetting gelation comprising a drug unstable to water is lyophilized to prevent any decomposition of the drug unstable to water and to thus provide a lyophilized pharmaceutical preparation stable over a long time period. Aqueous drug compositions having property of reversible thermosetting gelation for use in treatments of eyes, body cavities and skin can easily and quickly be reconstituted from the lyophilized pharmaceutical preparation through addition of an appropriate amount of a solvent for reconstitution. The reconstituted aqueous composition is a highly fluid liquid prior to the administration or application, causes gelation immediately after the administration or application to thus ensure an increase in the bioavailability of the effective component and a long acting drug efficacy.

TABLE 1

| Ex. No. | Composition Prior to Lyophilization | W/V% | Gelling Temp.[1] |
|---|---|---|---|
| 1 | Mitomycin | 0.04 | 32° C. |
|  | METOLOSE SM400 | 0.7 |  |
|  | METOLOSE SM15 | 0.7 |  |
|  | Citric Acid | 2.3 |  |
|  | PEG 4000 | 2.0 |  |
|  | 3N NaOH | to pH 8.0 |  |
|  | water | ad. 100 ml |  |
| 2 | Amphotericin B | 1.0 | 34° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 8.0 |  |
|  | water | ad. 100 ml |  |

TABLE 1-continued

| # | Component | Amount | Temp |
|---|---|---|---|
| 3 | Sodium Carbenicillin | 1.0 | 34° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 8.0 |  |
|  | water | ad. 100 ml |  |
| 4 | Sodium Cefazolin | 0.5 | 34° C. |
|  | METOLOSE SM400 | 0.7 |  |
|  | Metolose SM15 | 0.7 |  |
|  | Citric Acid 3Na.2H$_2$O | 3.5 |  |
|  | PEG 4000 | 2.0 |  |
|  | 1N HCl or 1N NaOH | to pH 6.5 |  |
|  | water | ad. 100 ml |  |
| 5 | Nystatin (4400 U/mg) | 0.1 | 34° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 8.0 |  |
|  | water | ad. 100 ml |  |
| 6 | Indometacin | 0.5 | 32° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 8.0 |  |
|  | water | ad. 100 ml |  |
| 7 | Acetylcholine Chloride | 1.0 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 6.0 |  |
|  | water | ad. 100 ml |  |
| 8 | Glutathion | 2.0 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 7.0 |  |
|  | water | ad. 100 ml |  |
| 9 | Pirenoxine | 0.005 | 34° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 6.5 |  |
|  | water | ad. 100 ml |  |
| 10 | Cyclophosphamide | 1.0 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 6.0 |  |
|  | water | ad. 100 ml |  |
| 11 | Dipivefrine | 0.05 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 5.0 |  |
|  | water | ad. 100 ml |  |
| 12 | Mitomycin C | 0.004 | 32° C. |
|  | METOLOSE SM15 | 2.1 |  |
|  | Citric Acid 3Na.2H$_2$O | 3.5 |  |
|  | PEG 20000 | 1.0 |  |
|  | 1N HCl or 1N NaOH | to pH 7.4 |  |
|  | water | ad. 100 ml |  |
| 13 | Mitomycin C | 0.004 | 36° C. |
|  | METOLOSE SM8000 | 0.2 |  |
|  | Citric Acid 3Na.2H$_2$O | 3.5 |  |
|  | PEG 6000 | 10 |  |
|  | 1N HCl or 1N NaOH | to pH 8.5 |  |
|  | water | ad. 100 ml |  |
| 14 | Mitomycin C | 0.004 | 36° C. |
|  | METOLOSE SM400 | 0.5 |  |
|  | Citric Acid 3Na.2H$_2$O | 3.5 |  |
|  | PEG 1000 | 9.0 |  |
|  | 1N HCl or 1N NaOH | to pH 7.0 |  |
|  | water | ad. 100 ml |  |
| 15 | Mitomycin C | 0.004 | 36° C. |
|  | METOLOSE SM8000 | 0.4 |  |
|  | Citric Acid 3Na.2H$_2$O | 2.9 |  |
|  | PEG 4000 | 13 |  |
|  | 1N HCl or 1N NaOH | to pH 8.0 |  |
|  | water | ad. 100 ml |  |
| 16 | Mitomycin C | 0.004 | 22° C. |
|  | METOLOSE SM1500 | 2.1 |  |
|  | Citric Acid 3Na.2H$_2$O | 1.8 |  |
|  | PEG 4000 | 13 |  |
|  | 1N HCl or 1N NaOH | to pH 8.0 |  |
|  | water | ad. 100 ml |  |
| 17 | Mitomycin C | 0.004 | 36° C. |
|  | METOLOSE SM15 | 2.1 |  |
|  | Citric Acid | 2.3 |  |
|  | PEG 50000 | 0.5 |  |
|  | Monoethanolamine | to pH 6.2 |  |
|  | water | ad. 100 ml |  |
| 18 | Mitomycin C | 0.004 | 34° C. |
|  | METOLOSE SM15 | 2.1 |  |
|  | Citric Acid | 1.2 |  |
|  | PEG 4000 | 6.0 |  |
|  | Triethanolamine | to pH 5.0 |  |
|  | water | ad. 100 ml |  |
| 19 | Mitomycin C | 0.004 | 36° C. |
|  | METOLOSE SM400 | 0.5 |  |
|  | Citric Acid | 2.3 |  |
|  | PEG 4000 | 6.0 |  |
|  | Diethanolamine | to pH 6.0 |  |
|  | water | ad. 100 ml |  |
| 20 | Mitomycin C | 0.004 | 36° C. |
|  | METOLOSE SM400 | 0.5 |  |
|  | Citric Acid | 2.3 |  |
|  | PEG 4000 | 6.0 |  |
|  | 1N KOH | to pH 7.5 |  |
|  | water | ad. 100 ml |  |
| 21 | Tetracycline hydrochloride | 0.5 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 6.0 |  |
|  | 1N HCl or 1N NaOH | to pH 3.0 |  |
|  | water | ad. 100 ml |  |
| 22 | Aspirin | 1.0 | 36° C. |
|  | METOLOSE SM400 | 0.7 |  |
|  | METOLOSE SM15 | 0.7 |  |
|  | Citric Acid 3Na.2H$_2$O | 3.5 |  |
|  | PEG 4000 | 2.0 |  |
|  | 1N HCl or 1N NaOH | to pH 6.0 |  |
|  | water | ad. 100 ml |  |

| Ex. No. | Amount Injected Prior to Lyophilization (ml) | Wt. (g) of Lyophilized Product | Solvent for Reconstitution | Amount of the Recon. Liq. (ml) | Gelling Temp. of Reconstituted prod. |
|---|---|---|---|---|---|
| 1. | 1.0 | 0.0655 | water | 1.0 | 32° C. |
| 2. | 1.0 | 0.0747 | water | 1.0 | 34° C. |
| 3. | 1.0 | 0.0748 | water | 1.0 | 34° C. |
| 4. | 1.0 | 0.0700 | water | 1.0 | 34° C. |
| 5. | 1.0 | 0.0660 | water | 1.0 | 34° C. |
| 6. | 1.0 | 0.0699 | Ag. soln. containing 0.17% boric acid, 0.11% borax, 0.2% polyoxyethylene hydrogenated castor oil 60 | 1.0 | 32° C. |
| 7. | 1.0 | 0.0754 | water | 1.0 | 36° C. |
| 8. | 1.0 | 0.0847 | 0.005% ag. soln. of benzalkonium chloride | 1.0 | 36° C. |
| 9. | 1.0 | 0.0648 | ag. soln. containing 0.026% of methylparaben, | 1.0 | 34° C. |

TABLE 1-continued

| Ex. No. | | | 0.014% of propylparaben | | |
|---|---|---|---|---|---|
| 10 | 1.0 | 0.0752 | water | 1.0 | 36° C. |
| 11 | 1.0 | 0.0658 | water | 1.0 | 36° C. |
| 12 | 1.0 | 0.0618 | water | 1.0 | 32° C. |
| 13 | 1.0 | 0.1333 | water | 0.9 | 36° C. |
| 14 | 1.0 | 0.1265 | water | 0.9 | 36° C. |
| 15 | 1.0 | 0.1597 | water | 0.9 | 36° C. |
| 16 | 1.0 | 0.1678 | water | 0.9 | 22° C. |
| 17 | 1.0 | 0.0711 | water | 1.0 | 36° C. |
| 18 | 1.0 | 0.1219 | water | 1.0 | 34° C. |
| 19 | 1.0 | 0.1263 | water | 1.0 | 36° C. |
| 20 | 1.0 | 0.1017 | water | 1.0 | 36° C. |
| 21 | 1.0 | 0.1109 | water | 1.0 | 36° C. |
| 22 | 1.0 | 0.0765 | water | 1.0 | 36° C. |

1)the gelling temperature prior to the lyophilization.

TABLE 2

| Ex. No. | Rate (%) of Residual Drug in Lyophilized Product After Storing at 40° C. for 1 Month | Rate (%) of Residual Drug in Composition Prior to Lyophilization at 40° C. for 1 Month |
|---|---|---|
| 1 | 77.8 | 19.3 |
| 3 | 82.4 | 1.8 |
| 4 | 94.2 | 1.9 |
| 6 | 89.0 | 15.2 |
| 8 | 96.6 | 0.0 |
| 9 | 94.5 | 4.6 |
| 21 | 78.2 | 0.0 |
| 22 | 90.4 | 0.0 |

We claim:

1. A lyophilized pharmaceutical preparation having property of reversible thermosetting gelation obtained by lyophilizing an aqueous composition comprising an effective amount of a drug. 0.2 to 2.1 (W/V)% of methylcellulose wherein the methoxyl group of the methylcellulose is within the range of 26 to 33%, 1.2 to 2.3 (W/V)% of citric acid and 0.5 to 13 (W/V)% of polyethylene glycol.

2. The lyophilized pharmaceutical preparation according to claim 1 for ophthalmic use wherein the pharmaceutically effective drug is selected from the group consisting of antiviral agents, antifungal agents, antibacterial substances, antiallergic agents, anti-inflammatory agents, miotics, vitamins, antiglaucoma drugs, anticataract drugs, carbonic anhydrase inhibitors, immunosuppressive agents, amino acids, adjuvants for surgery, anti-proliferative agents for fibroblast and mixture thereof.

3. The lyophilized pharmaceutical preparation according to claim 2 wherein the drug is selected from the group consisting of adenosine arabinoside, interferons, Amphotericin B, Nystatin, Carbenicillin, Penicillin G, Cefazolin, Tetracycline, Polymyxin B, Vancomycin, Amikacin, Erythromycin, Aspirin, Indomethacin, Acetylcholine, Physostigmine, Cocarboxylase, Cobamamide, Dipivefrine, Glutathione, Pirenoxine, Acetazolamide, Methotrexate, Cyclophosphamide, cysteine, hyaluronidase, α-Chymotrypsin, Mitomycin C and pharmaceutically acceptable salts thereof.

4. The lyophilized pharmaceutical preparation according to claim 3 wherein the drug is Mitomycin C.

5. The lyophilized pharmaceutical preparation according to claim 1 for local or dermatological use wherein the pharmaceutically effective drug is selected from the group consisting of antifungal agents, antibacterial substances and anti-inflammatory agents.

6. The lyophilized pharmaceutical preparation according to claim 5 wherein the drug is selected from the group consisting of Nystatin, Tetracycline, Amikacin, Polymyxin B, Erythromycin, Aspirin, Indomethacin and pharmaceutically acceptable salts thereof.

7. The lyophilized pharmaceutical preparation according to claim 1 to be administered into body cavities wherein the pharmaceutically effective drug is selected from the group consisting of antiviral agents, antifungal agents, antibacterial substances, antipyretics, analgesics, anti-inflammatory agents and antineoplastics.

8. The lyophilized pharmaceutical preparation according to claim 7 wherein the drug is selected from the group consisting of interferons, Nystatin, Tetracycline, Amikacin, Erythromycin, Aspirin, Indomethacin, Doxorubicin, Asparaginase and pharmaceutically acceptable salts thereof.

9. The lyophilized pharmaceutical preparation according to claim 1 wherein a 2.0% aqueous solution of the methylcellulose has a viscosity, as determined at 20° C., ranging from 13 to 12000 millipascal-sec.

10. The lyophilized pharmaceutical preparation according to claim 1 wherein the polyethylene glycol has a weight-average molecular weight ranging from 1000 to 50,000.

11. The lyophilized pharmaceutical preparation according to claim 1 wherein the aqueous composition having property of reversible thermosetting gelation reconstituted with a solvent for reconstitution has a gelling temperature of from about 20° C. to about 40° C. and the composition is liquid at a temperature lower than the gelling temperature.

12. The lyophilized pharmaceutical preparation according to claim 1 wherein it includes at least one of pharmaceutically acceptable buffers, preservatives and solubilizing agents.

13. The lyophilized pharmaceutical preparation according to claim 1 wherein the solvent for reconstitution is water or water containing at least one of pharmaceutically acceptable buffers, preservatives and solubilizing agents.

14. A lyophilized pharmaceutical preparation comprising about 1 to about 50% by weight of methylcellulose, about 5 to about 60% by weight of citric acid or a salt thereof (expressed in terms of the reduced amount of citric acid), about 3 to about 88% by weight of polyethylene glycol and about 0.004 to about 70% by weight of a drug.

* * * * *